(12) United States Patent
Mazur et al.

(10) Patent No.: US 8,294,891 B2
(45) Date of Patent: Oct. 23, 2012

(54) NON-INVASIVE OPTICAL ANALYSIS USING SURFACE ENHANCED RAMAN SPECTROSCOPY

(75) Inventors: Eric Mazur, Concord, MA (US); Eric Diebold, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 505 days.

(21) Appl. No.: 12/523,567

(22) PCT Filed: Jan. 22, 2008

(86) PCT No.: PCT/US2008/051643
§ 371 (c)(1),
(2), (4) Date: Feb. 22, 2010

(87) PCT Pub. No.: WO2008/091858
PCT Pub. Date: Jul. 31, 2008

(65) Prior Publication Data
US 2010/0171949 A1 Jul. 8, 2010

Related U.S. Application Data

(60) Provisional application No. 60/886,270, filed on Jan. 23, 2007, provisional application No. 60/886,256, filed on Jan. 23, 2007, provisional application No. 60/962,538, filed on Jul. 30, 2007.

(51) Int. Cl.
*G01N 21/03* (2006.01)
*G01J 3/44* (2006.01)
(52) U.S. Cl. ............... 356/301; 356/239.1; 356/239.4; 436/165
(58) Field of Classification Search ............ 356/301, 356/239.1–240.1; 436/165
See application file for complete search history.

(56) References Cited

U.S. PATENT DOCUMENTS
4,965,430 A 10/1990 Curtis et al.
(Continued)

FOREIGN PATENT DOCUMENTS
DE 202004008333 8/2004
(Continued)

OTHER PUBLICATIONS

Keller S, et al., "Quality control of food with near-infrared-excited Raman spectroscopy" Fresenius Journal of Analytical Chemistry, vol. 346, Jun. 1993, pp. 863-867.

(Continued)

*Primary Examiner* — Layla Lauchman
(74) *Attorney, Agent, or Firm* — Nutter McClennen & Fish LLP; Thomas J. Engellenner; Reza Mollaaghababa

(57) ABSTRACT

In one aspect, a system for use in product packaging is disclosed that includes a polymeric sensing substrate coupled to a package such that a front sensing surface thereof is in contact with a portion of a product, e.g., a fungible product, stored in the package and a back surface thereof is accessible via an environment external to the package. The system further includes a radiation source adapted to direct radiation to the substrate's back surface such that the radiation would interact with one or more molecular species of the product that are in contact with the substrate's sensing surface. The system also includes a detector that is adapted to detect radiation returning from the substrate in response to its illumination by the radiation source. The front surface of the sensing substrate can comprise a plurality of micron-sized or submicron-sized ridges having a discontinuous or continuous metal coating, e.g., a metallic layer with a thickness in a range of about 10 nm to about 1000 nm (and preferably in a range of about 50 nm to about 120 nm), disposed thereon.

21 Claims, 13 Drawing Sheets

U.S. PATENT DOCUMENTS

| | | | |
|---|---|---|---|
| 5,534,068 | A | 7/1996 | Beach et al. |
| 5,538,674 | A | 7/1996 | Nisper et al. |
| 5,557,409 | A | 9/1996 | Downer et al. |
| 6,376,177 | B1 | 4/2002 | Poponin |
| 6,406,777 | B1 | 6/2002 | Boss et al. |
| 7,057,256 | B2 | 6/2006 | Carey, III et al. |
| 7,242,469 | B2 * | 7/2007 | Wang et al. ............... 356/301 |
| 7,354,792 | B2 | 4/2008 | Carey, III et al. |
| 7,384,792 | B1 * | 6/2008 | Wang et al. ............... 436/165 |
| 7,428,046 | B2 * | 9/2008 | Wang et al. ............... 356/301 |
| 7,790,469 | B2 * | 9/2010 | Wang et al. ............... 436/165 |
| 2002/0149769 | A1 | 10/2002 | Roorda et al. |
| 2003/0029495 | A1 | 2/2003 | Mazur et al. |
| 2003/0059820 | A1 | 3/2003 | Vo-Dinh |
| 2003/0213715 | A1 | 11/2003 | Klepac et al. |
| 2004/0101469 | A1 | 5/2004 | Demers |
| 2004/0150818 | A1 | 8/2004 | Armstrong et al. |
| 2004/0162554 | A1 | 8/2004 | Lee et al. |
| 2004/0163758 | A1 | 8/2004 | Kagan et al. |
| 2005/0112544 | A1 | 5/2005 | Xu et al. |
| 2006/0038990 | A1 | 2/2006 | Habib et al. |
| 2006/0079062 | A1 | 4/2006 | Mazur et al. |
| 2006/0158653 | A1 | 7/2006 | Chiarello et al. |
| 2006/0209413 | A1 | 9/2006 | Kim et al. |
| 2006/0246573 | A1 | 11/2006 | Kurane et al. |
| 2006/0292778 | A1 * | 12/2006 | Sekiguchi ............... 438/197 |
| 2007/0115469 | A1 | 5/2007 | Ebstein |
| 2009/0033929 | A1 | 2/2009 | Mazur et al. |

FOREIGN PATENT DOCUMENTS

| | | |
|---|---|---|
| EP | 1382459 | 1/2004 |
| EP | 1416325 | 5/2004 |
| EP | 1731962 | 12/2006 |
| WO | 02077608 | 10/2002 |
| WO | 2006060734 | 6/2006 |
| WO | 2006086014 | 8/2006 |
| WO | 2006138442 | 12/2006 |
| WO | 2007060989 | 5/2007 |
| WO | 2008091852 | 7/2008 |
| WO | 2008091858 | 7/2008 |

OTHER PUBLICATIONS

Montoya, et al., "Detection of Salmonella using Surfaced Enhanced Raman Scattering" Chemical and Biological Sensing IV, Proceedings of SPIE, vol. 5085, Apr. 21, 2003, pp. 144-152.

Liu, et al., "Nanowell surface enhanced Raman scattering arrays fabricated by soft-lithography for label-free biomolecular detections in integrated microfluidics," 2005 American Institute of Physics, Applied Physics Letters 87 (3 pages).

Stuart, et al., "Biological applications of localised surface plasmonic phenomenae", 20050201; 20050200, vol. 152, No. 1, pp. 13-32, XP006023676.

Jung, et al., "Facile fabrication of large area nanostructures for efficient surface-enhanced Raman scattering," J. Mater. Chem., 2006, 16, 3145-3149.

Kneipp, et al., "Population Pumping of Excited Vibrational States by Spontaneous Surface-Enhanced Raman Scattering," The American Physical Society, Physical Review Letters, vol. 76, No. 14, Apr. 1, 1996, pp. 2444-2447.

Lehmann, J. et al., "Excimer Laser Micro Machining of Inorganic Dielectrics" Applied Surface Science, Elsevier, Amsterdam, NL, vol. 106, Oct. 1, 1996, pp. 282-286, XP000879307 ISSN: 0169-4332.

Xia, Q. et al., "Ultrafest Patterning of Nanostructures in Polymers Using Laser Assisted Nanoimprint Lithography" Applied Physics Letters, AIP, American Institute of Physics, Melville, NY, vol. 83, No. 21, Nov. 24, 2003, pp. 4414-4419, XP001191757, ISSN: 003-6951.

International Search Report and Written Opinion dated Aug. 14, 2008 for PCT/US2008/051643.

International Search Report and Written Opinion dated Aug. 14, 2008 for PCT/US2008/051647.

Ru, et al., "Surface Enhanced Raman Scattering Enhancement Factors: A Comprehensive Study," J. Phys. Chem. C. 2007, 111, 13794-13803.

Vo-Dinh, Surface-Ehanced Rama Spectrometry With Silver Particles on Stochasitc-Post Substrates, Analytica Chimica Acta, 1986, 139-148, vol. 181.

Vo-Dinh et al., Plasmonics-Based Nanostructures for Surface-Enhanced Raman Scattering Bioanalysis, Methods in Molecular Biology, 2005, 255-283, vol. 300.

Henley et al., Excimer laser nanostructuring of nickel thin films for the catalytic growth of carbon nanotubes, Applied Physics Letters, 2004, 4035, 84.

Henley et al., Laser-Nanostructured Ag Films as Substrates for Surface-Enhanced Raman Spectroscopy, Applied Physics Letters, 2006, 081904, 88.

Lehmann, et al., Fabrication of submicron crossed square wave gratings by dry etching and thermoplastic replication techniques, Journal of Vacuum Science Technology, Oct.-Dec. 1983, pp. 1207-1210, vol. 1, No. 4.

Nie et al., Probing Single Molecules and Single Nanoparticles by Surface-Enhanced Raman Scattering, Science Feb. 21, 1997, pp. 1102-1106, vol. 275.

Campion, et al., Surface-enhanced Raman scattering, Chemical Society Reviews, 1998, pp. 241-250, vol. 27.

Kneipp, et al., Ultrasenstive Chemical Analysis by Raman Spectroscopy, Chemical Review, 1999, pp. 2957-2975, vol. 99.

Emory, et al., Direct Observation of Size-Dependent Optical Enhancement in Single Metal Nanoparticles, Journal of American Chemical Society, 1998, pp. 8009-8010, vol. 120.

Kottmann, et al., Plasmon resonant coupling in metallic nanowires, Optics Express, Jun. 4, 2001, pp. 655-663, vol. 8, issue 12.

Jiang, et al., Single Molecule Raman Spectroscopy at the Junctions of Large Ag Nanocrystals, Journal of Physical Chemistry, 2003, pp. 9964-9972, vol. 107.

Genov, et al., Resonant Field Enhancements from Metal Nanoparticle Arrays, Nano Letters, 2004, pp. 153-158, vol. 4, issue 1.

Cao, et al., Nanoparticles with Raman Spectroscopic Fingerprints for DNA and RNA Detection, Science, Aug. 30, 2002, pp. 1536-1340, vol. 297.

Liu, et al., Nanopillar Substrates for SERS, Proceedings of the 7th International Conf. on Miniaturized Chemical and Biochemical Analysis Systems, Oct. 5-9, 2003, pp. 705-708.

Liu, et al., Cinfigurable 3D Nanoscale High Aspect Ratio Pillars for Surface-Enhanced Raman Spectroscopy IEEE 2003, pp. 425-427.

Liu et al., Nanowell surface enhanced Raman scattering arrays fabricated by soft-lithography for label-free biomolecular detections in integrated microfluidics, Applied Physics Letters, 2005, pp. 074101-1-074101-3, vol. 87.

Duyne, et al., Atomic force microscopy and surface-enhanced Raman spectroscopy I. Ag island films and Ag film over polymer nanosphere surfaces supported on glass, Journal of Chemical Physics, Aug. 1, 1993, pp. 2101-2115, vol. 99, issue 3.

Quagliano, The SERS Effect as a Tool for Studying Molecules Absorbed on Semiconductor Surfaces, The Internet Journal of Vibrational Spectroscopy, 2004, vol. 4, Edition 2.

Drachev, et al., Adaptive silver films towards bio-array applications, Proc. of SPIE vol. 5703.

Haynes, et al., Nanosphere Lithography: A Versatile Nanofabrication Tool for Studies of Size-Dependent Nanoparticle Optics, Journal of Physical Chemistry, 2001, pp. 5599-5611, vol. 105, Issue 24.

Zhang, et al., An electrochemical surface-enhanced Raman spectroscopy approach to anthrax detection, Proc. of SPIE, vol. 5221, pp. 82-91.

Drachev, et al., Adaptive Silver Films for Detection of Antibody-Antigen Binding, 2005, pp. 8368-8373, vol. 21, Issue 18.

Lyandres, et al., Real-Time Glucose Sensing by Surface-Enhanced Raman Spectroscopy in Bovine Plasma Facilitated by a Mixed Decanethiol/Mercaptohexanol Partition Layer, Analytical Chemistry, Oct. 1, 2005, pp. 6134-6139, vol. 77, Issue 19.

Fagano, et al., Raman Spectroscopic Study of the Avidin-Biotin Complex, Journal of Raman Spectroscopy, 1995, pp. 991-995, vol. 26.

Duyne, et al., Spatially Resolved Surface Enhanced Raman Spectroscopy: Feasibility, Intensity Dependence on Sampling Area and Attomole Mass Sensitivity, May 2, 1986, pp. 190-196, vol. 126, issue 2.

Drachev, et al, Surface-Enhanced Raman Difference between Human Insulin and Insulin Lispro Detected with Adaptive Nanostructures, Journal of Physical Chemistry, 2004, pp. 18046-18052, vol. 108.

Kneipp, et al., Single Molecule Detection Using Surface-Enhanced Raman Scattering (SERS), Physical Review Letters, Mar. 3, 1997, pp. 1667-1670, vol. 78, issue 9.

Haynes, et al., Plasmon Scanned Surface-Enhanced Raman Scattering Excitation Profiles, Materials Research Society Symposia Proceedings, 2002, p. 7.1-7.6, vol. 728.

Her, et al., Femtosecond laser-induced formation of spikes on silicon, Applied Physicals A. Materials Science & Processing, 2000, pp. 383-385, vol. 70.

Shen, et al., Femtosecond laser-induced formation of submicrometer spikes on silicon in water, Applied Physicals Letters, Dec. 6, 2004, pp. 5694-5696, vol. 85, issue 23.

Shen, et al., Formation of regular arrays of siliconmicrospikes by femtosecond laser irradiation through a mask, Applied Physics Letters, pp. 1715-1717, vol. 82, issue 11.

Laibinis, et al., Comparison of the Structures and Wetting Properties of Self-Assembled Monolayers of n-Alkanethiols on the Coinage Metal Surfaces, Cu, Ag, Au, Journal of the American Chemical Society, 1991, pp. 7152-7167, vol. 113.

Sockalingum, et al., Raman and SERS spectroscopy for probing drug-target interactions: from in-vitro models to intracellular imaging, Internet Journal of Vibrational Spectroscopy.

Astilean, et al., Ordered Metallic Nanostructures for Surface-Enhanced Raman Spectroscopy, Romanian Reports in Physics, 2004, pp. 346-351, vol. 56, issue 3.

Bergman, et al., Relationship between surface-enhanced Raman scattering and the dielectric properties of aggregared silver films, Optics Letters, Jan. 1981, pp. 33-35, vol. 6, issue 1.

Katayama, et al., Formation of ring patterns surrounded by ripples by single-shot laser irradiation with ultrashort pulse width at the solid/liquid interface, Applied Physics Letters, Jun. 16, 2003, pp. 4244-4246, vol. 82, No. 24.

Sylvia, et al., Surface-Enhanced Raman Detection of 2,4-Dinitrotoleune Impurity Vapor as a Marker to Locate Landmines, Analytical Chemistry, Dec. 1, 2000, pp. 5834, 5840, vol. 72.

Quagilano, et al., The SERS Effect as a Tool for Studying Molecules Adsorbed on Semiconductor Surfaces, The Internet Journal of Vibrational Spectroscopy, vol. 4, Ed. 2 (2004).

Office Action dated Mar. 23, 2009 for U.S. Appl. No. 12/017,720.

* cited by examiner

EXAMPLE RAMAN SPECTRUM OF A BENZENETHIOL SAM ON H-PDMS, COLLECTED WITH THE BACK ILLUMINATION CONFURATION. THE INTEGRATION (COLLECTION) TIME WAS 1 SECOND.

HPDMS MOLD OF NANOSTRUCTURED Si, COATED W/ 80nm Ag
BENZENETHIOL SAM APPLIED- FRONT ILLUMINATION

NON-INVASIVE OPTICAL ANALYSIS USING SURFACE ENHANCED RAMAN SPECTROSCOPY

RELATED APPLICATIONS

The present application claims priority to the following provisional applications, which are herein incorporated by reference in their entirety:

"Non-Invasive Optical Analysis Using Surface Enhanced Raman Spectroscopy," filed on Jan. 23, 2007 and having a Ser. No. 60/886,270, "Polymeric Substrates for Raman Spectroscopy," filed on Jan. 23, 2007 and having a Ser. No. 60/886,256, "Metalized Semiconductor Substrates for Raman Spectroscopy" that was filed on Jul. 30, 2007 and having a Ser. No. 60/962,538.

BACKGROUND

The present invention relates generally to optical systems and methods for obtaining information regarding the interior of a package and/or a product contained therein.

A variety of products, e.g., fungible food products, are stored in packages for shipping to customers. Many of such packaged products have a limited shelf life. As such, the time lag between packaging and consumption, or other environmental factors, can result in spoilage of the product. Further, the process of packaging itself can result in contamination of the product. Many of conventional techniques for examining a packaged product can, however, adversely affect the package or the product.

Accordingly, there is a need for systems and methods for obtaining information about a packaged product non-invasively, e.g., without adversely affecting the package and/or the product. There is also a need for obtaining information about the interior of a package (container), e.g., to ensure it is not contaminated.

SUMMARY

In one aspect, a system for use in product packaging is disclosed that includes a sensing substrate coupled to a package such that a front sensing surface thereof is in contact with, or in proximity of, a portion of a product, e.g., a fungible product, stored in the package and a back surface thereof is accessible via an environment external to the package. The system further includes a radiation source adapted to direct radiation to the substrate's back surface such that the radiation would interact with one or more molecular species of the product that are in contact with the substrate's sensing surface. The system also includes a detector that is adapted to detect radiation returning from the substrate in response to its illumination by the radiation source. The front surface of the sensing substrate can comprise a plurality of micron-sized or submicron-sized ridges having a metallic coating. In some cases, the metallic coating is in the form of a substantially continuous layer, e.g., one with a thickness in a range of about 10 nm to about 1000 nm (and preferably in a range of about 50 nm to about 120 nm), disposed thereon. In some other cases, the metallic coating is in the form of a discontinuous metal coating that covers some portions of the underlying surface but leaves other portions uncovered.

In a related aspect, the system includes an analyzer that can operate on the detected radiation to determine one or more characteristics of the product stored in the package. For example, when a food product is stored in the package, the analyzer can determine whether the food product is suitable for consumption. By way of example, the analyzer can include a Raman spectrometer operating on the returning radiation to generate one or more Raman spectra of at least one constituent of the product. In some cases, the analyzer can include a memory module for storing the acquired spectra, as well as one or more reference spectra. In addition, the analyzer can include instructions, e.g., in the form of executable software code, for comparing the acquired spectra with the reference spectra to determine certain characteristics of the product.

In another aspect, an identification tag, e.g., in the form of an optically readable tag, such as a bar code, can be disposed on an external surface of the package for identifying the product stored therein.

In another aspect, a method of non-invasively determining a characteristic of a product stored in a package is disclosed that includes coupling a polymeric sensing substrate to the package such that a sensing surface of the substrate is in contact with, or in proximity of, the product and an opposed surface of the substrate is accessible via an environment external to the package. Radiation from an external source can be directed to the accessible surface such that the radiation, after traversing at least a portion of the polymeric substrate, would interact with one or more constituents of the product in contact with, or in proximity of the sensing surface. At least a portion of the radiation returning from the substrate can be detected and analyzed to determine a characteristic of the product. In some cases, the detected radiation is analyzed, e.g., by a Raman spectrometer, to determine Raman shifts, thereby generating one or more Raman spectra of the constituents of the stored product interacting with the radiation.

In another aspect, the invention provides an optical sensing system that includes a chamber adapted for containing an analyte, and a polymeric substrate having a structured conductive surface (e.g., in the form of plurality of ridges and a metallic coating (e.g., a continuous or discontinuous coating) covering at least a portion of those ridges) on a front side thereof. The substrate is coupled to the chamber such that at least a portion of the conductive surface is exposed to the chamber and at least a portion of a back side of the substrate (a side opposed to the conductive surface) is accessible via an environment external to the chamber. The system can further include a radiation emitter optically coupled to the chamber so as to direct radiation to the accessible portion of the substrate's back side. A detector coupled to the chamber detects at least a portion of radiation returning from the substrate in response to illumination by the emitter.

In some cases, the radiation directed to the substrate has one or more wavelengths suitable for inducing surface enhanced Raman scattering by one or more Raman active constituents of a portion of the analyte that is in contact with, or in proximity of, the substrate's metallic coating. The detector can detect the Raman scattered radiation so as to generate one or more Raman spectra of the Raman active constituents.

In another aspect, a package for storing a product is disclosed that comprises an enclosure and a sensing substrate, e.g., a polymeric sensing substrate, coupled to the enclosure such that a front sensing surface of the substrate faces the interior of the enclosure and an opposed back surface of the substrate is accessible via an environment external to the enclosure. The sensing surface can comprise a conductive surface formed, e.g., by a metallic coating, e.g., a metallic layer having a thickness in a range of about 10 nm to about 1000 nm or a discontinuous metallic coating, exhibiting micron-sized, and preferably submicron-sized, ridges. In some cases, an identification tag, e.g., a bar code, is disposed on an external surface of the package to provide information about the product stored therein.

Further understanding of the invention can be obtained by reference to the following detailed description in conjunction with the associated drawings, which are briefly described below.

DETAILED DESCRIPTION

Figure 1:
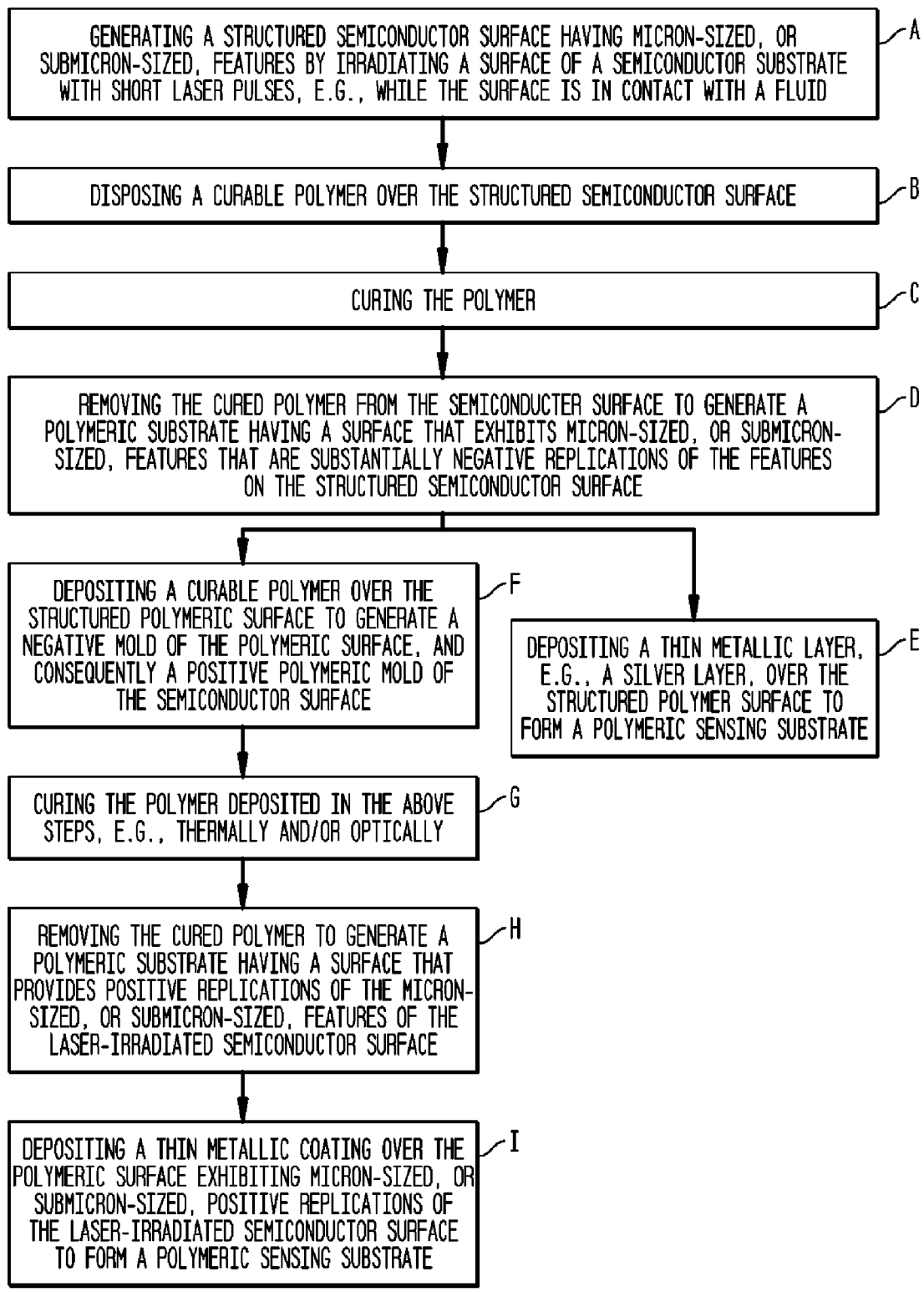
FIG. 1 is a flow chart depicting various steps for fabricating polymeric sensing substrates suitable for use in various embodiments of the optical systems of the invention, FIG. 2 schematically depicts an exemplary apparatus suitable for generating micron-sized or submicron-sized structures on a substrates' surface, such as a semiconductor surface.

The present invention generally provides systems and methods for non-invasively determining selected properties of a product, e.g., a fungible product such as a food product, stored in a package. Many such systems employ a polymeric substrate coupled to a package in which the product is stored to spectroscopically, e.g., via SERS, interrogate the product, thereby determining one or more selected properties thereof and/or obtaining information regarding the interior of the package. The polymeric substrate can include a surface exhibiting microns-sized, and preferably submicron-sized, structures (surface undulations) (e.g., in the form of spikes) having amplitudes less than about a few microns (e.g., less than about 20 microns), and preferably less than about 1 micron, and more preferably less than about 100 nanometers (e.g., in a range of about 1 nm to about 50 nm). The structured surface is metalized, e.g., with a thin layer of a metal, e.g., silver or gold, having a thickness in a range of about 10 nm to about 1000 nm (and preferably in a range of about 50 nm to about 120 nm) or a discontinuous metal coating, to form a structured conductive surface over the polymeric surface. The term "structured surface," as used herein, refers to a surface that exhibits undulations (e.g., spikes) with peak-to-trough excursions (amplitudes) of a few microns (e.g., less than about 20 microns), and preferably less than about 1 micron, and more preferably less than about 100 nm (e.g., in a range of about 1 nm to about 50 nm). The "structured surface" can exhibit a surface roughness with amplitudes less than about 1 micron, and preferably less than about 100 nanometers, and more preferably less than about 50 nm.

Prior to describing various exemplary embodiments of the optical systems according to the teachings of the invention, exemplary methods of fabricating polymeric substrates suitable for use in many embodiments of such optical systems are discussed. In particular, with reference to a flow chart 10 shown in FIG. 1, an exemplary method for fabricating a polymeric substrate, e.g., one suitable for use in an optical system of the invention, comprises generating a structured surface (step A) by irradiating a mold surface (e.g., a surface of a semiconductor, or a glass, or a metal substrate) with a plurality of short laser pulses. The term "short laser pulses," as used herein, refers to laser pulses having durations less about a few nanoseconds ($10^{-9}$ seconds), e.g., pulses with durations in a range of about 100 femtoseconds ($10^{-15}$ seconds) to about one picosecond ($10^{-12}$ seconds). By way of example, in some embodiments, a silicon substrate can be exposed to a plurality of short pulses (e.g., pulses having durations in a range of about 100 femtoseconds to about 500 femtoseconds) while the surface is in contact with a fluid, e.g., water. The pulses cause a change in surface topography characterized by surface undulations (e.g., spikes) having amplitudes less than about a few microns (e.g., less than about 10 microns), and preferably less than 1 micron, e.g., in a range of about 50 nm to about 200 nanometers.

Figure 2:
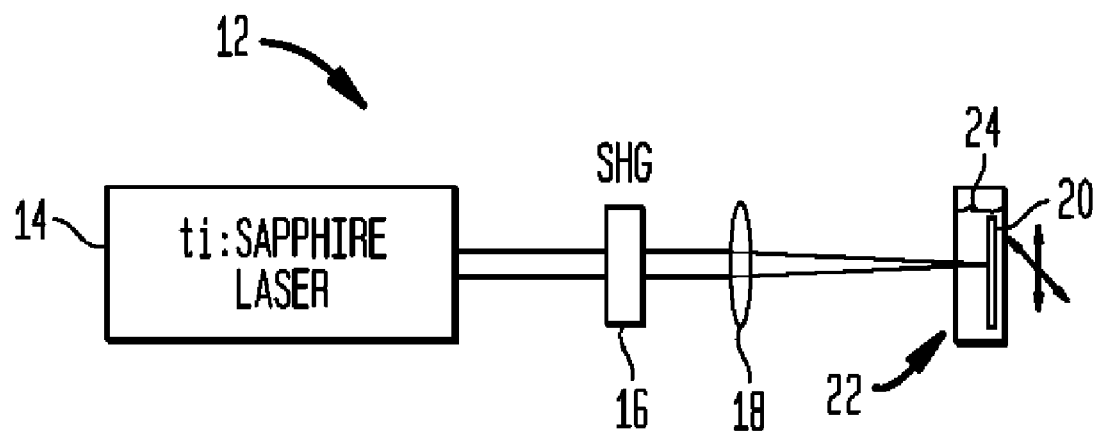

By way of example, FIG. 2 schematically depicts an exemplary optical system 12 suitable for processing a mold substrate (e.g., a semiconductor substrate) so as to generate micron-sized, and preferably submicron-sized, features (structures) on a surface thereof. For example, the features can include a plurality of spikes, e.g., substantially columnar structures extending from the surface to a height above the surface. The optical system 12 includes a Titanium-Sapphire (Ti:Sapphire) laser 14 for generating short laser pulses. By way of example, the Ti:Sapphire laser can generate laser pulses with a pulse width of about 80 femtoseconds at 800 nm wavelength (e.g., at an average power of 300 mW and at a repetition rate of 95 MHz). The pulses generated by the Ti:Sapphire laser can be applied to a chirped-pulse regenerative amplifier (not shown) that, in turn, can produce, e.g., 0.4 millijoule (mJ)), 100 femtosecond pulses at a wavelength of 800 nm and at a repetition rate of about 1 kilohertz.

The optical system 12 further includes a harmonic generation system 16 that receives the amplified pulses and doubles their frequency to produce, e.g., 100-femtosecond second-harmonic pulses at a wavelength of 400 nanometers. A lens 18 focuses the second-harmonic pulses onto a surface of a semiconductor sample 20, which can be disposed on a three-dimensional translation system (not shown). A glass liquid cell 22 can be coupled to the semiconductor sample so as to allow the sample surface exposed to the pulses to have contact with a liquid 24 (e.g., water) contained within the cell. Further details regarding methods and apparatuses for generating microns-sized, and preferably submicron-sized, features on a semiconductor surface can be found in co-pending U.S. patent application entitled "Femtosecond Laser-Induced Formation Of Submicrometer Spikes On A Semiconductor Substrate" having a Ser. No. 11/196,929, filed Aug. 4, 2005, which is herein incorporated by reference. U.S. Pat. No. 7,057,256 entitled "Silicon-Based Visible And Near-Infrared Optoelectronic Devices" and Published U.S. Patent Application No. 2003/00299495 entitled "Systems And Methods For Light Absorption and Field Emission Using Microstructured Silicon," both of which are herein incorporated by reference, provide further disclosures regarding microstructuring silicon surfaces by application of short laser pulses.

Figure 3:
FIG. 3 shows nanosized structures, in the form of spikes, formed on silicon surface by exposing a silicon substrate's surface to a plurality of femtosecond pulses while the surface is in contact with water, FIG. 4A schematically shows (not to scale) a micro- or nanostructured semiconductor surface on which a curable polymer is disposed.

By way of illustration, FIG. 3 shows a silicon surface on which a plurality of nanosized features are generated via irradiation of the surface with a plurality of femtosecond laser pulses while the surface was in contact with water.

Figure 4A:
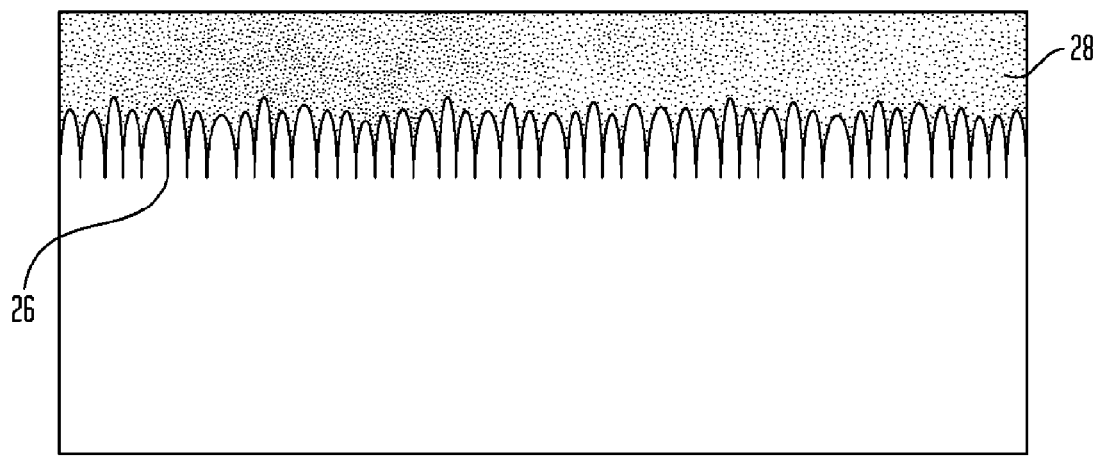
FIG. 4B shows (not to scale) a polymeric substrate having a surface exhibiting micro- or nanosized ridges, where the polymeric substrate can be formed by curing the curable polymer shown in FIG. 4A and separating the cured polymer from the underlying semiconductor surface, FIG. 4C schematically shows (not to scale) the polymeric substrate of FIG. 4B with a thin metallic layer deposited over its structured surface such that the metallic layer exhibits undulations substantially corresponding to the structures on the underlying polymeric surface.
FIG. 4D is a schematic side view (not to scale) of a polymeric substrate according to an embodiment of the invention having a structured surface on which a discontinuous metal coating is disposed.
FIG. 4E is a perspective view of the polymeric substrate of FIG. 4D, FIG. 5A schematically shows (not to scale) a curable polymer disposed over the structured surface of the polymeric substrate shown in FIG. 4B, FIG. 5B schematically shows (not to scale) a polymeric substrate obtained by curing the curable polymer shown in FIG. 5A, FIG. 5C schematically shows (not to scale) a polymeric sensing substrate in accordance with an embodiment of the invention formed by depositing a thin metallic layer over the polymeric substrate shown in FIG. 5B, FIG. 6A schematically depicts a system according to an embodiment of the invention for non-invasively interrogating a product contained within a container, FIG. 6B schematically depicts a container according to the teachings of the invention to which a polymeric sensing substrate is coupled, FIG. 7A schematically depicts (not to scale) a metal-coated semiconductor sensing substrate suitable for use in some embodiments of the optical systems of the invention, FIG. 7B schematically depicts a top view of a metalized structured surface illustrating surface gaps that introduce discontinuities in the metal coating, which is characterized by a plurality of metalized regions and gaps between those regions, FIG. 7C provides a schematic perspective view of the metalized surface shown in FIG. 7B, illustrating the metalized regions, which are formed by a plurality of metal particles deposited on the structures of the surface, as well as gaps between different metalized regions.

Referring again to the flow chart 10 of FIG. 1 as well as FIG. 4A, subsequent to forming micron-sized, and preferably submicron-sized, features on a mold substrate's surface 26 (e.g., a semiconductor substrate), in step B, a curable polymer 28 can be disposed (e.g., poured) over that surface, e.g., as a monolayer film. The polymer can be cured (step C), e.g., thermally and/or optically, to generate a negative mold of that surface, which provides negative replications of the semiconductor surface structures including the submicron-sized undulations of the underlying semiconductor surface. In some embodiments, prior to disposing the polymer on the surface, a surfactant, such as (tridecafluoro-1,1,2,2-tetrahydroocty)-1-trichlorosilane, is applied to the surface to facilitate the subsequent removal of the cured polymer as a negative mold of the surface. In some embodiments, the polymer is cured by applying heat thereto for a selected time period. By way of example, the polymer can be exposed to a temperature in a range of about 15° C. to about 100° C. for a time duration in a range of about 1 minute to about 48 hours. In other embodiments, an optically curable polymer can be employed that can be cured by exposure to radiation, e.g., UV radiation. In many cases, the curing process causes cross-linking of the polymer, thereby generating a polymeric substrate that retains its shape.

In general, a variety of curable polymers can be employed for generating the mold. In many embodiments, the curable polymer is a thermoplastic polymer that can be readily cured to retain its shape. Some examples of such polymers include, without limitation, hard-poly(dimethylsiloxane) (H-PDMS), or poly(dimethylsiloxane) (PDMS). In other embodiments, optically curable polymers, such as photoresists, SU-8, or polyurethane, can be employed.

Figure 4B:
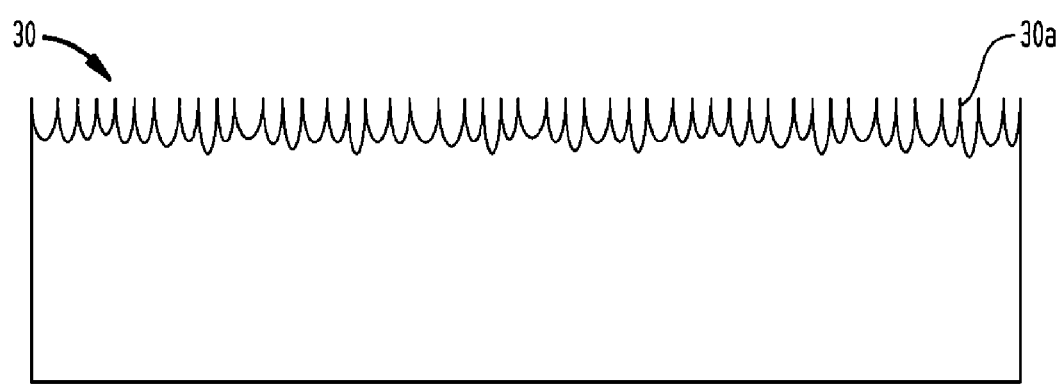

Subsequent to curing the polymer, the cured polymer can be removed from the substrate surface (step D), e.g., by employing standard methods including the application of a salinization compound in some cases to assist with the separation process, to generate a polymeric substrate 30 having a surface 30a that is substantially a negative mold of the structured mold surface (e.g., a structured semiconductor surface), as shown schematically in FIG. 4B. In other words, the polymeric substrate's surface 30a exhibit microns-sized, and preferably submicron-sized, features (undulations) that are substantially negative replications of the structures on the substrate surface. By way of example, the spikes on the polymer surface substantially correspond to the hollow volumes between the spikes on the semiconductor nanostructured surface. The features of the substrate's surface 30a have preferably sizes (e.g., heights) that are less than about 1 micron (e.g., in a range of about 1 to about 100 nanometers, and preferably in a range of about 1 nm to about 50 nm).

Figure 4C:
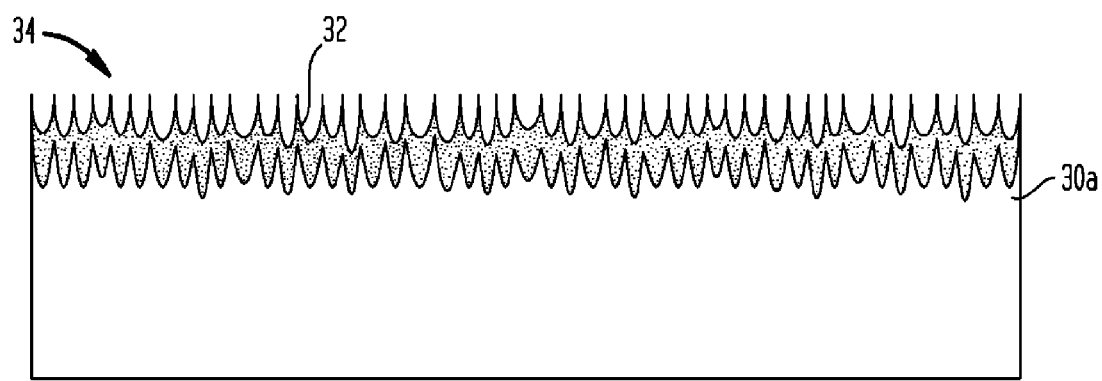

With continued reference to the flow chart 10 as well as FIG. 4C, in some embodiments, in a subsequent step (E), a thin metallic coating 32, e.g., silver, is disposed on the structured surface 30a of the polymeric substrate 30 to produce a sensing substrate 34 suitable for use in many embodiments of the optical systems according to the teachings of the invention. In some embodiments of the invention, the metallic coating 32 is in the form of a metallic layer that has a thickness in a range of about 10 nm to about 1000 nm, and more preferably in a range of about 50 nm to about 120 nm. The metallic surface is deposited over the polymeric substrate such that the resulting metallic layer would exhibit micron-sized, and preferably submicron-sized, undulations that correspond substantially to the structures on the underlying polymeric surface. In other words, the metallic layer provides a structured conductive surface (e.g., a conductive surface exhibiting micron-sized, and preferably submicron-sized, structures).

Figure 4D:
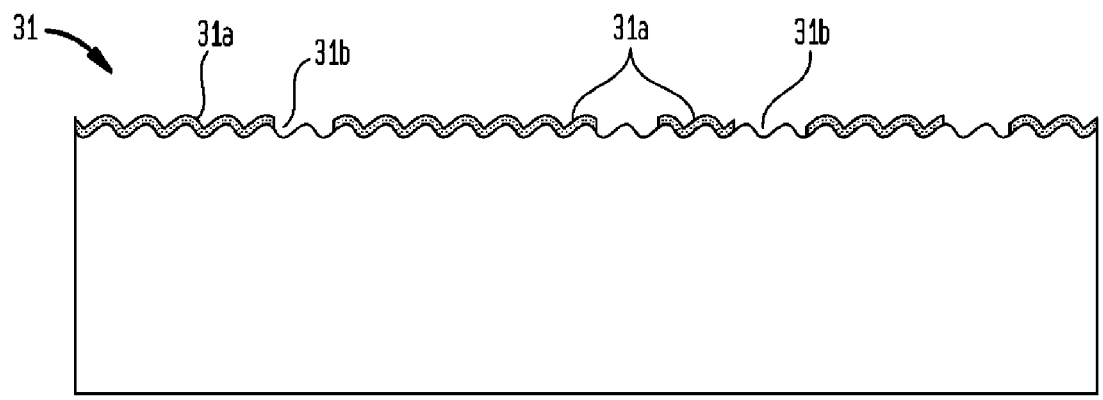
Figure 4E:
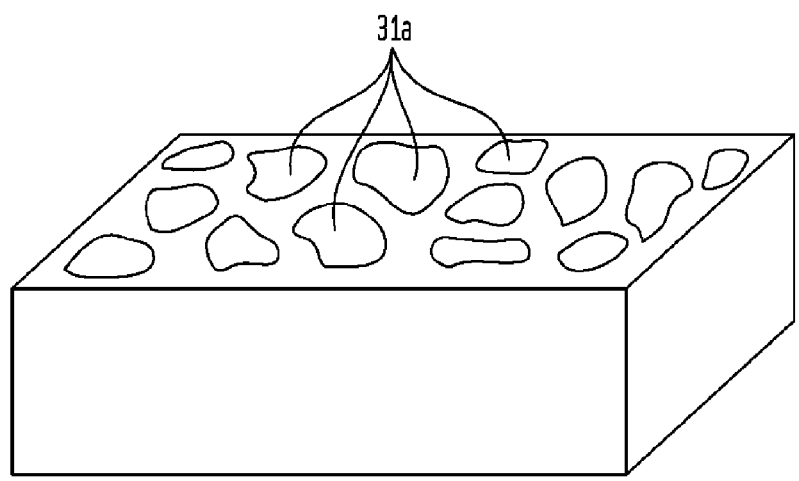

With reference to FIG. 4D, in some embodiments, rather than depositing a continuous metallic layer over the structured polymeric surface, a discontinuous metal coating 31 is disposed over that surface. As shown schematically in FIG. 4D, the discontinuous metal coating 31 can include a plurality of metallic regions 31a, e.g., in the form of aggregates of metal particles, covering portions of the underlying polymeric surface with a plurality of gaps 31b that leave the respective portions of the polymeric surface exposed. In some cases, the surface gaps can have submicron-sized lateral dimensions, e.g., an average lateral dimension of a gap can be of the order of tens of nanometers. The metallic regions can exhibit micron-sized and/or submicron-sized undulations, e.g., similar to those of the underlying polymeric surface.

Such discontinuous metal coatings can be generated, e.g., by evaporating a metal over the polymeric surface. By way of example, the amount of metal deposited on the polymeric structured surface can be controlled (e.g., by adjusting the evaporation rate and the deposition time) so as to form surface gaps in the metal coating, e.g., to generate a non-uniform coating punctuated by non-metalized portions. By way of example, in some cases, the quantity of the deposited metal on the structured polymeric surface can correspond to a quantity that would produce a uniform metal coating on a putative smooth surface (a surface lacking the aforementioned micron-sized or submicron-sized features) of the same polymeric material having the same macroscopic dimensions as that of the structured polymeric surface with a thickness in a range of about 50 nm to about 500 nm, or in a range of about 50 nm to about 200 nm, or in a range of about 50 nm to about 80 nm.

The resulting substrate can be used in a variety of applications, e.g., SERS. In some cases, regions in proximity of the surface gaps, e.g., nanosized gaps between metalized portions, can correspond to regions of large SERS enhancement.

Figure 5A:
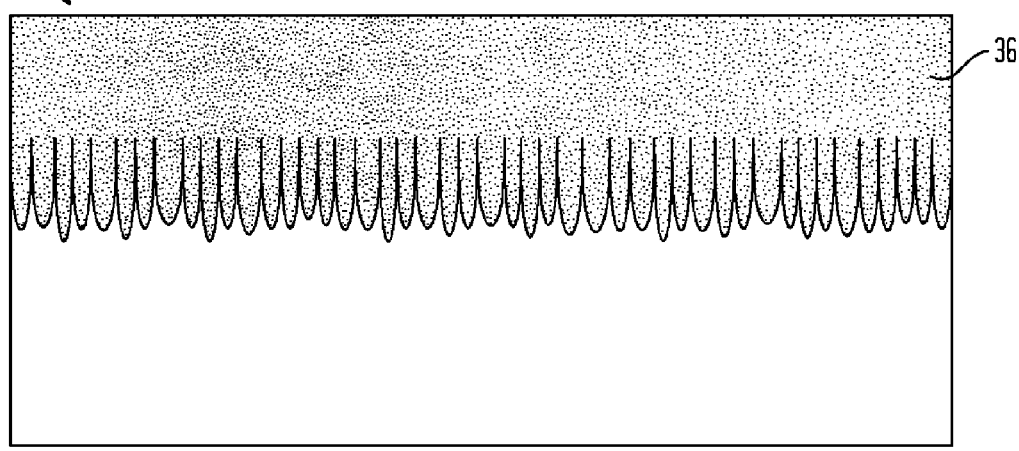
Figure 5B:
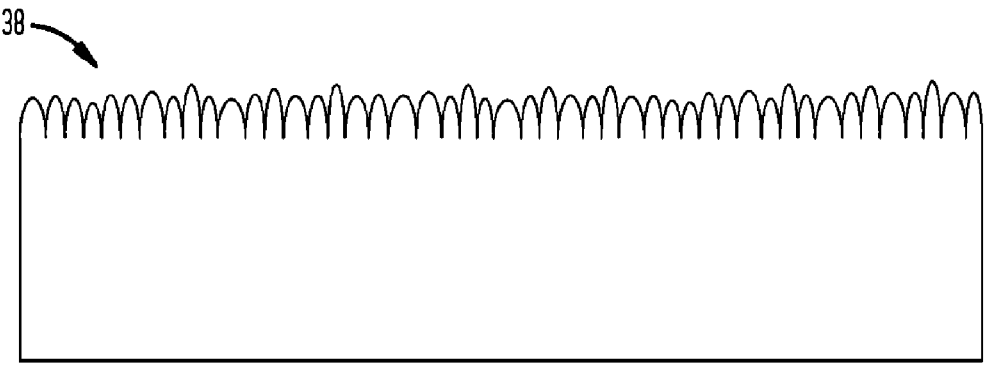

Alternatively, in some other embodiments, the negative polymeric mold is employed to fabricate a polymeric substrate having a surface that exhibits positive replications of the microns-sized, and preferably submicron-sized, features of the laser-irradiated semiconductor substrate surface. By way of example, as indicated in step (F) of the flow chart 10 and as shown schematically in FIG. 5A, a curable polymer 36 can be poured over the surface of the aforementioned polymeric substrate 30 (e.g., as a monolayer film), which has a surface that exhibits negative replications of the structured semiconductor surface, so as to fill the submicron-sized (and in some cases micron-sized) surface depressions. The curable polymer 36 can then be cured (step G) and separated from the polymeric substrate (step H) to generate another polymeric substrate 38. Similar to the curable polymer utilized to form the negative mold, the curable polymer 36 can be a thermally and/or an optically curable polymer, such as those listed above.

In many embodiments, however, the curable polymer 36 is selected to be different from the polymer from which the negative mold is formed so as to facilitate their separation after the polymer 36 is cured. Further, in some embodiments, a surfactant is applied to the negative mold polymeric surface to facilitate the separation of the two polymeric substrates after polymer 36 is cured. In some embodiments, the polymer 36 can be cured via a heat treatment, e.g., via exposure to a temperature in a range of about 15° C. to about 100° C. for a time duration in a range of about 1 minute to about 48 hours. In some other embodiments in which polymer 36 is optically curable, it can be cured by exposure to appropriate radiation, e.g., UV radiation.

Figure 5C:
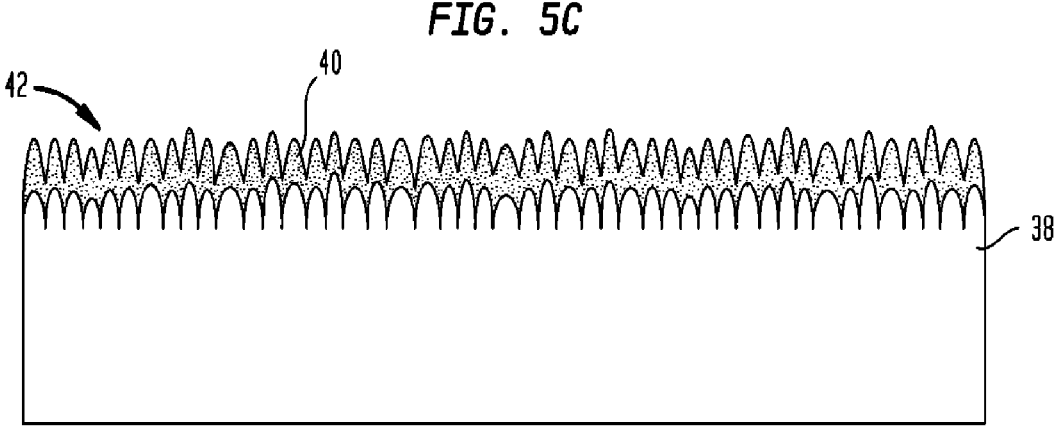

Referring again to the flow chart 10 as well as FIG. 5C, subsequently in step (I), a thin metallic layer 40, e.g., silver or gold, can be disposed on the structured surface of polymeric substrate 38 having microns-sized, or submicron-sized, structures to generate a polymeric sensing substrate 42, which is suitable for use in surface enhanced Raman Spectroscopy. The thickness of the metallic layer can be in a range of about 10 nm to about 1000 nm, and preferably in a range of about 50 nm to about 120 nm. In some cases, a discontinuous metal coating can be formed on the structured surface of the polymeric substrate 38, e.g., in a manner discussed above.

Figure 6A:
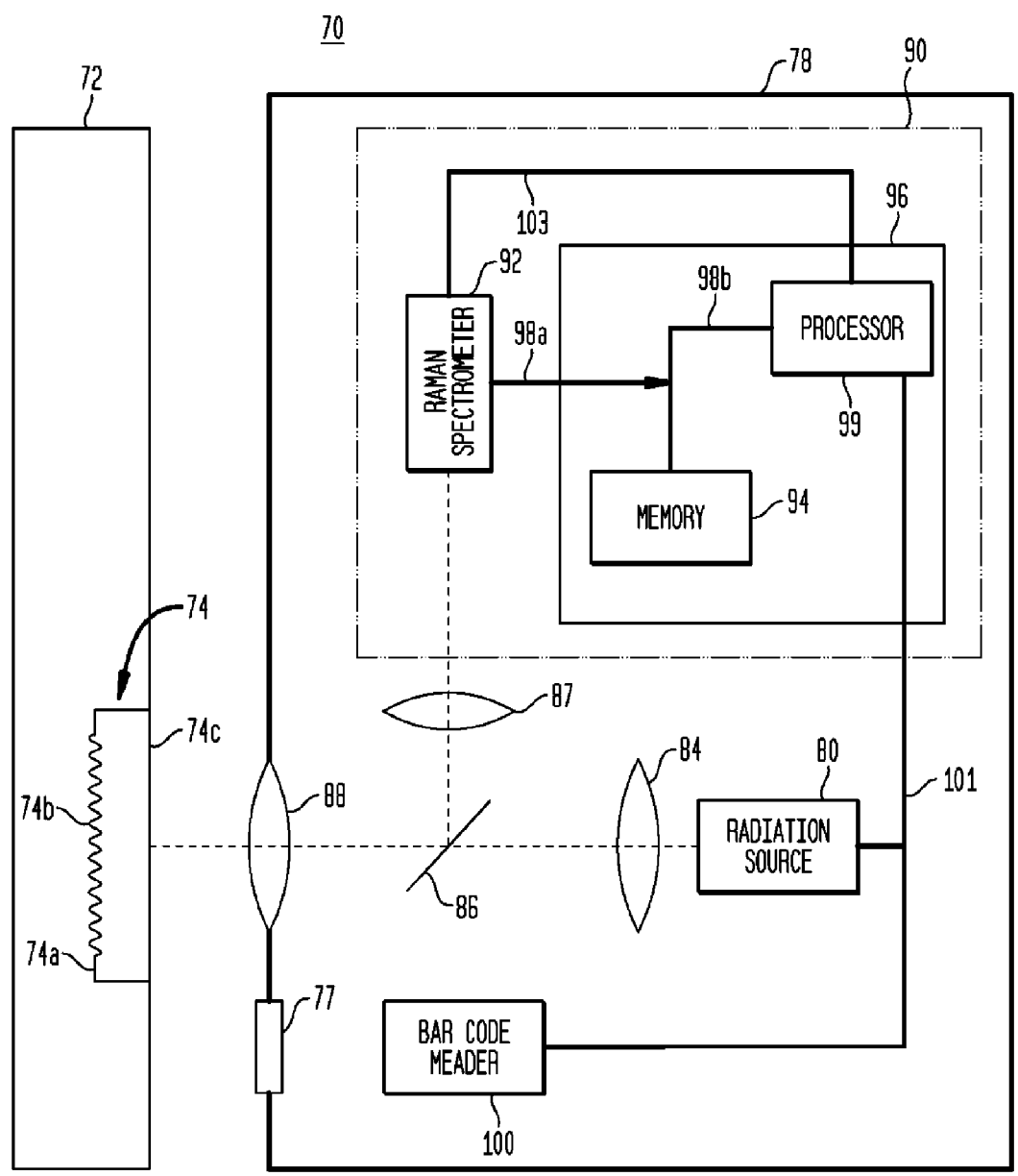

In some embodiments, systems for non-invasively obtaining information about a product, e.g., a fungible product such as food, stored within a package, and/or the interior environment of the package, e.g., in the absence of the product, are provided that employ the above polymeric sensing substrates. By way of example, FIG. 6A schematically depicts an embodiment of such a system 70, which includes a package 72 for containing a food product, e.g., milk, to which sensing substrate 74 is coupled. The sensing substrate can be formed as a polymeric substrate, such as one of the above substrates 34 or 72, having a surface 74a exhibiting a plurality of microns-sized, and preferably submicron-sized, ridges 74b covered with a thin metallic layer, e.g., in a manner discussed above. The sensing substrate is coupled to the package 72 such that the metal-covered ridges face the interior of the package to be in contact with a food, or other fungible, product stored in the package, while an opposed surface 74c of the sensing substrate is accessible via the external environment. The term "in contact with" can refer not only to physical contact but also to being in proximity of a product such that the field-enhancing effects of a sensing substrate surface (the metal-covered surface) are discernable. For example, in some cases, a thin dielectric layer may cover the sensing surface. In many embodiments, the sensing substrate is coupled to the package so as to form a seal (e.g., a hermetic seal) therewith, so as to prevent exposure of the product contained in the package to the external environment (e.g., to prevent oxidation of the product). As shown schematically in FIG. 6B, the package 72 can further include a bar code 76, or other product identifier, that can identify the type of the product stored in the package. Without any loss of generality, in the following description, the product stored in the package is assumed to be a food product, though the teachings of the invention can be applicable to other products stored within a container.

The system 70 further includes a optical device 78 that can non-invasively probe the food product stored within the package to determine selected properties thereof, e.g., whether it is suitable for consumption. The optical device 78 includes a radiation source 80 that can generate radiation with one or more wavelengths suitable for exciting the Raman active modes of one or more molecular constituents of the food product stored within the package. By way of example, the radiation source can be a laser, such as, a HeNe laser or a solid-state laser, such as a semiconductor diode laser, or any other suitable radiation source. The radiation source can operate in a continuous or a pulsed mode. The radiation generated by the source can be directed via one or more optical components to the polymeric sensing substrate 74 that is coupled to the package. In this embodiment, the optical components comprise a collimator lens 84 that directs the radiation through a beam splitter 86 to a focusing lens 88 that, in turn, focuses the radiation onto the sensing substrate 74. More specifically, the probe radiation that is directed to the back surface 74c of the substrate 74 and passes therethrough to activate one or more Raman active modes of a portion of the food (or other fungible) product in contact with, or in proximity of, the metalized (e.g., via a continuous or a discontinuous metal coating) structured surface of the substrate (the polymeric sensing substrate is substantially transparent to the probe radiation, thereby allowing back illumination of the substrate to excite one or more Raman active modes of molecular species that are in contact with, or in proximity of, its conductive surface).

The radiation returning from the substrate that carries the Raman signatures associated with the activated Raman modes is directed via the lens 88 to the beam splitter 86, which in turn sends the radiation via a convergent lens 87 to a detection/analysis module 90 that can derive selected information about the food product based on the Raman signatures carried by the returning radiation.

More specifically, in this exemplary embodiment, the detection/analysis module 90 includes a Raman spectrometer 92 that receives the returning radiation and generates one or more Raman spectra of the food (or other fungible) product, which can be stored in a memory module 94. A variety of Raman spectrometers, such as slit-based or fiber-coupled spectrometers, can be employed.

A diagnostic module 96 in communication with the Raman spectrometer 92 receives data corresponding to the one or more Raman spectra generated by the spectrometer and analyzes that data to determine selected information regarding the product stored in the package, e.g. in a manner discussed below. The various components of the detection/analysis module can communicate via one or more buses, such as communications buses 98a and 98b.

Figure 6B:
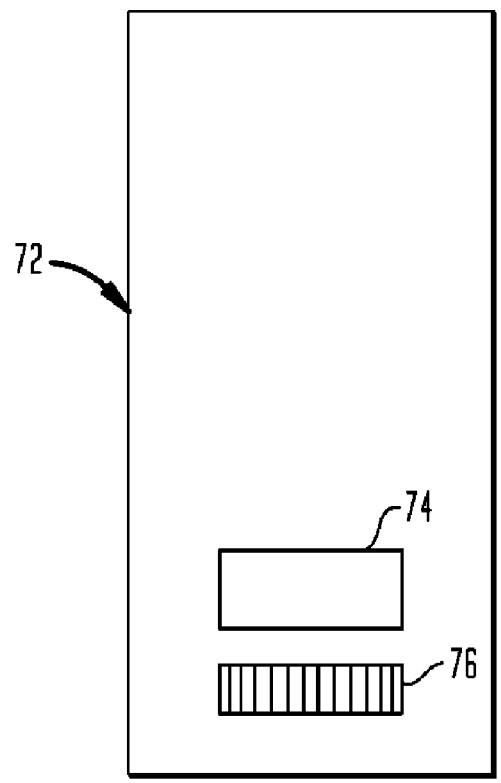

With continued reference to FIGS. 6A and 6B, in many embodiments, the analysis module initially determines the type of food product stored in the package. By way of example, in this embodiment, a bar-code reader 100 can scan the bar code 76 printed on the package, via radiation transmitted through a window 77, and can send the bar code data to the diagnostic module 96. The diagnostic module 96 can compare the bar code data with reference data stored in the device (e.g., the form of a table), for example, in the memory module 94, to determine the type of product that is stored in the package.

The diagnostic module can then access one or more reference Raman spectra for the identified product previously stored in the device, e.g., in the memory module 94, with the one or more Raman spectra obtained for the product presently stored in the package to determine selected properties of the stored product. For example, when examining a package containing milk, one or more Raman spectra of the milk under examination can be compared with reference Raman spectra corresponding to fresh milk; milk that is a few days old; milk that is on the verge of going bad, and spoiled milk, to determine whether the examined milk is suitable for consumption.

A processor 99 can control operation of the device and can further provide the computational capability needed by the detection/analysis module 90. For example, the processor can send control signals, e.g., via a bus 101, to the bar code reader and the radiation source to control their operation. For example, the processor can initially activate the bar code reader to determine the type of product stored in the package, and subsequently trigger the radiation source to obtain one or more Raman spectra of the product. In addition, in this example, the processor can send control signals to the Raman spectrometer (e.g., via a bus 103), for example, to activate the spectrometer in synchrony with the triggering of the radiation source.

Alternatively, or in addition, the above methods and systems of the invention can be utilized to investigate the interior environment of a package, e.g., to determine whether it is free of certain contaminants. For example, in the above system 70, the package 72 in the absence of the product can be examined via Raman spectroscopy, e.g., in a manner discussed above, to determine whether it contains one or more contaminants, at least at concentrations that would lead to discernible Raman spectra. In particular, the device 78 can be employed to obtain Raman spectra of one or more Raman active constituents (e.g., gases) present in the interior of the package. These Raman spectra can be compared with known spectra of selected contaminants, previously stored in the device, to determine if the contaminants are present in the package.

With continued reference to FIG. 6A, in some embodiments, the optical device 78 includes a handheld housing 78a in which the various components of the device, such as those discussed above, are disposed. By way of example, such a handheld device can be readily utilized in a food production facility to examine food packages as a quality control measure.

Figure 7A:
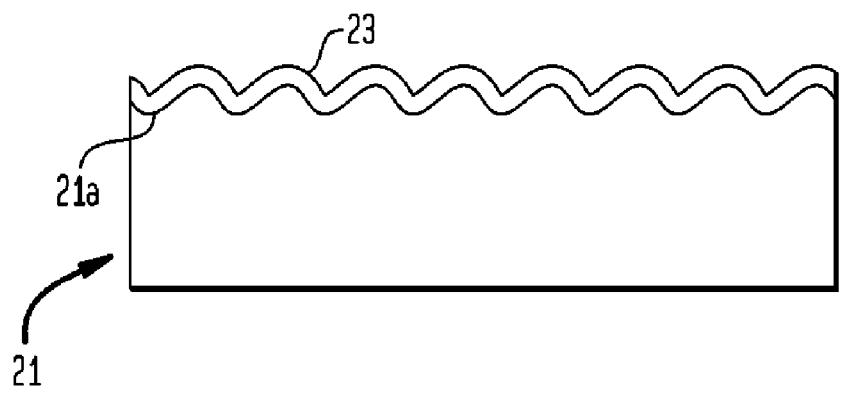

In some embodiments, rather utilizing a polymeric sensing substrate, a semiconductor substrate having a structured surface coated with a thin metallic coating (e.g., a continuous or discontinuous metal coating) can be utilized as the sensing substrate. By way of example, FIG. 7A shows such a silicon substrate 21 having a structures surface 21a (a surface exhibiting micron-sized or preferably submicron-sized structures) on which a thin metal layer 23 (e.g., a metal layer having a thickness in a range of about 10 nm to about 1000 nm, and preferably in a range of about 50 nm to about 120 nm) is deposited. The structured silicon surface can be formed in a manner discussed above (by exposure to short laser pulses), and the metal layer can be formed over the surface by any suitable method, such as evaporation and electrodeposition.

Figure 7B:
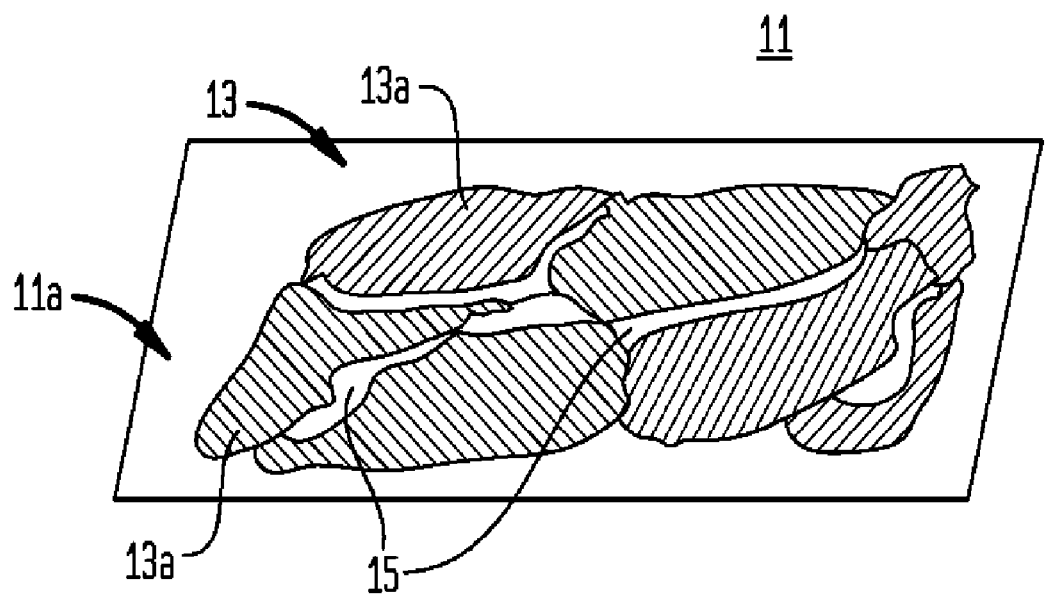
Figure 7C:
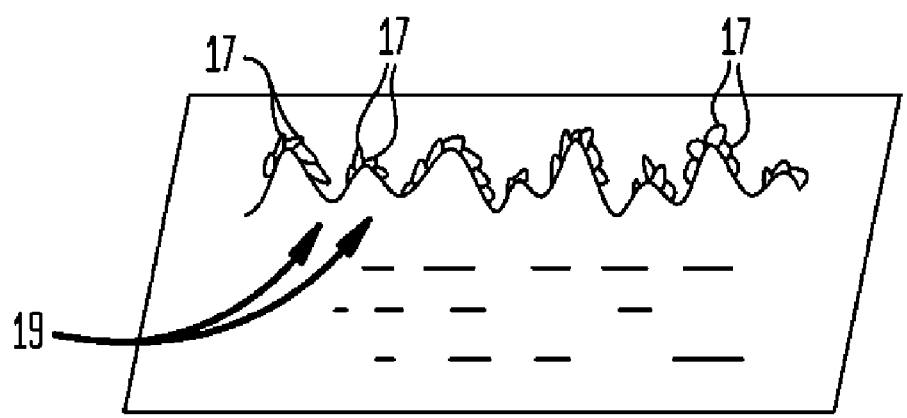

In some cases, the structured semiconductor surface can be coated with a discontinuous metal coating to provide a sensing substrate. As shown schematically in FIGS. 7B and 7C, such a substrate 11, e.g., a semiconductor substrate such as a silicon substrate, can include a structured surface 11a formed, for example, by exposure of the surface to short laser pulses (e.g., pulses with durations in a range of about 10 femtoseconds to about 500 femtoseconds) while the surface is in contact with a fluid (e.g., water). A discontinuous metal coating 13 is disposed over the structured surface, e.g., by evaporating a metal onto the surface. The discontinuous metal coating 13 can include one or more metalized regions 13a, e.g., in the form of aggregates of metal particles, with a plurality of the surface portions 15 (gaps between the metalized regions) remaining unmetalized. In other words, rather than having a uniformly thick metal coating that covers the entire surface, the metalized surface can be characterized by aggregates of metal particles 17 that are deposited on the structured surface (e.g., on the tips and sides of the micron-sized or submicron-sized structures protruding above the surface as well as on troughs between the peaks) as well as a plurality of surface gaps 19 that are substantially devoid of the metal particles. In some embodiments, the metal particles forming the metalized coating regions can have average sizes less than about 1 micron, or less than about 500 nm, or less than about 100 nm.

By way of example, in some cases, the quantity of the deposited metal on the structured substrate surface can correspond to a quantity that would produce a uniform metal coating on a putative smooth surface (a surface lacking the aforementioned micron-sized or submicron-sized features) of the same material having the same macroscopic dimensions as that of the structured surface with a thickness in a range of about 50 nm to about 500 nm, or in a range of about 50 nm to about 200 nm, or in a range of about 50 nm to about 80 nm.

Further details regarding semiconductor substrates having such metalized structured surfaces can be found in the copending U.S. patent application entitled "Metalized Semiconductor Substrates for Raman Spectroscopy," which claims priority to a provisional application with the same title filed on Jan. 23, 2007 and having a Ser. No. 60/886,244 and "Semiconductor Substrates for Raman Spectroscopy Having Discontinuous Metal Coatings," which claims priority to aforementioned provisional patent application entitled "Metalized Semiconductor Substrates for Raman Spectroscopy" that was filed on Jul. 30, 2007 and having a Ser. No. 60/962,538, which are concurrently filed with the present application. Both of these applications are herein incorporated by reference in their entirety.

The semiconductor (e.g., silicon) substrate can then be coupled to a package such that its structured metallic surface faces the interior of the package to be in contact with, or in proximity of, a product contained in the package, and its opposed back surface is accessible via the external environment. The thickness of the substrate and/or the wavelength of the probe radiation can be selected such that the radiation would penetrate the substrate to excite one or more Raman-active constituents in contact with, or in proximity of, the metalized surface. The returning radiation can be analyzed, for example, in a manner discussed above to obtain information about the product and/or the interior of the package (e.g., in the absence of the product).

The following examples illustrate various sensing substrates having submicron-sized structured conductive surfaces, such as the polymeric substrates discussed above, can enhance the signal-to-noise ratio in SERS, and are hence particularly suited for use in the optical systems of the invention. It should, however, be understood that the examples are not intended to necessarily indicate the optimal results (e.g., optimal signal-to-noise ratios) that can be achieved by employing such substrates, or the full range of analytes that can be examined.

EXAMPLE 1

Figure 8A:
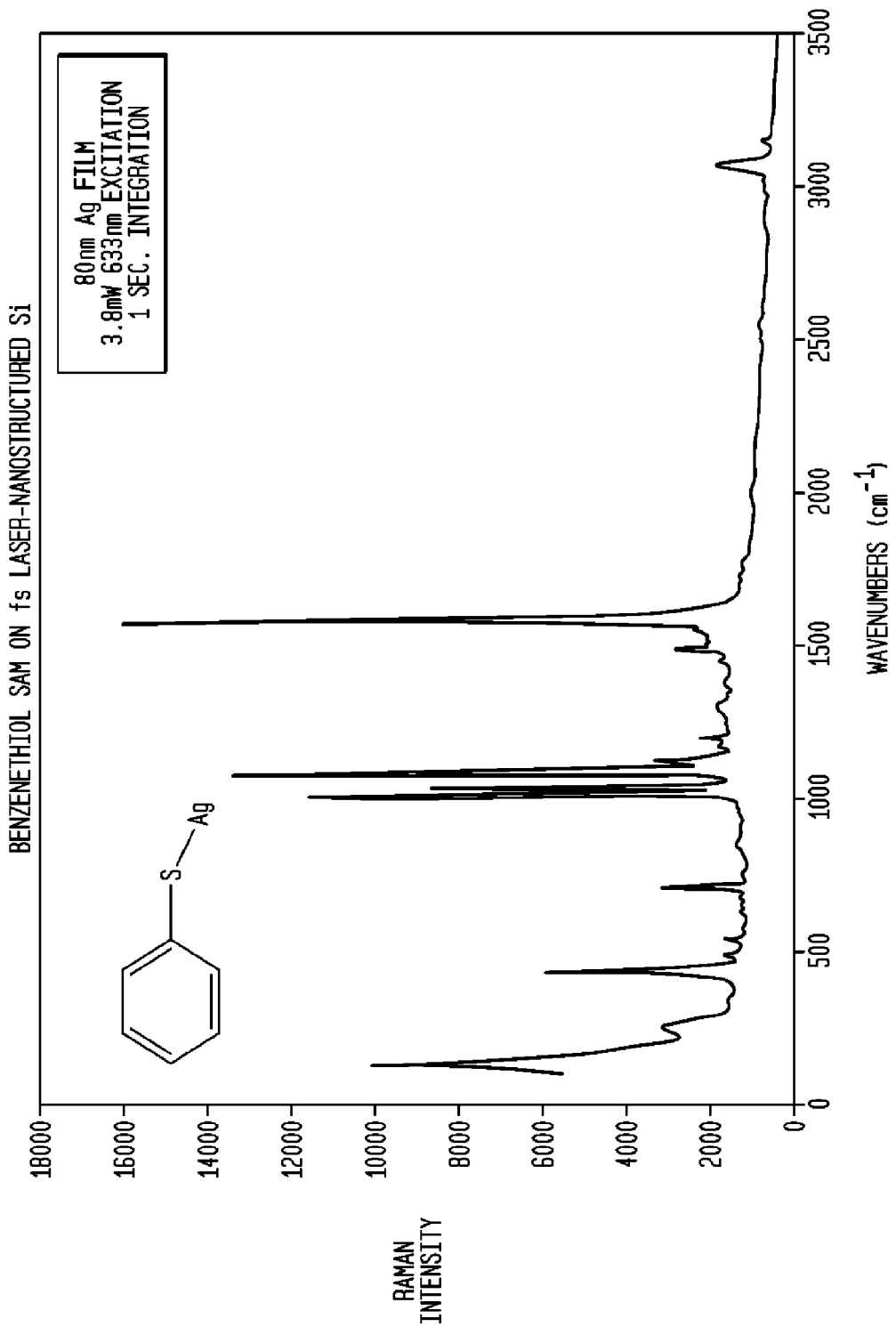
FIG. 8A is a surface enhanced Raman spectrum of a film of Benzenethiol disposed over a metal-covered structured silicon surface.
Figure 8B:
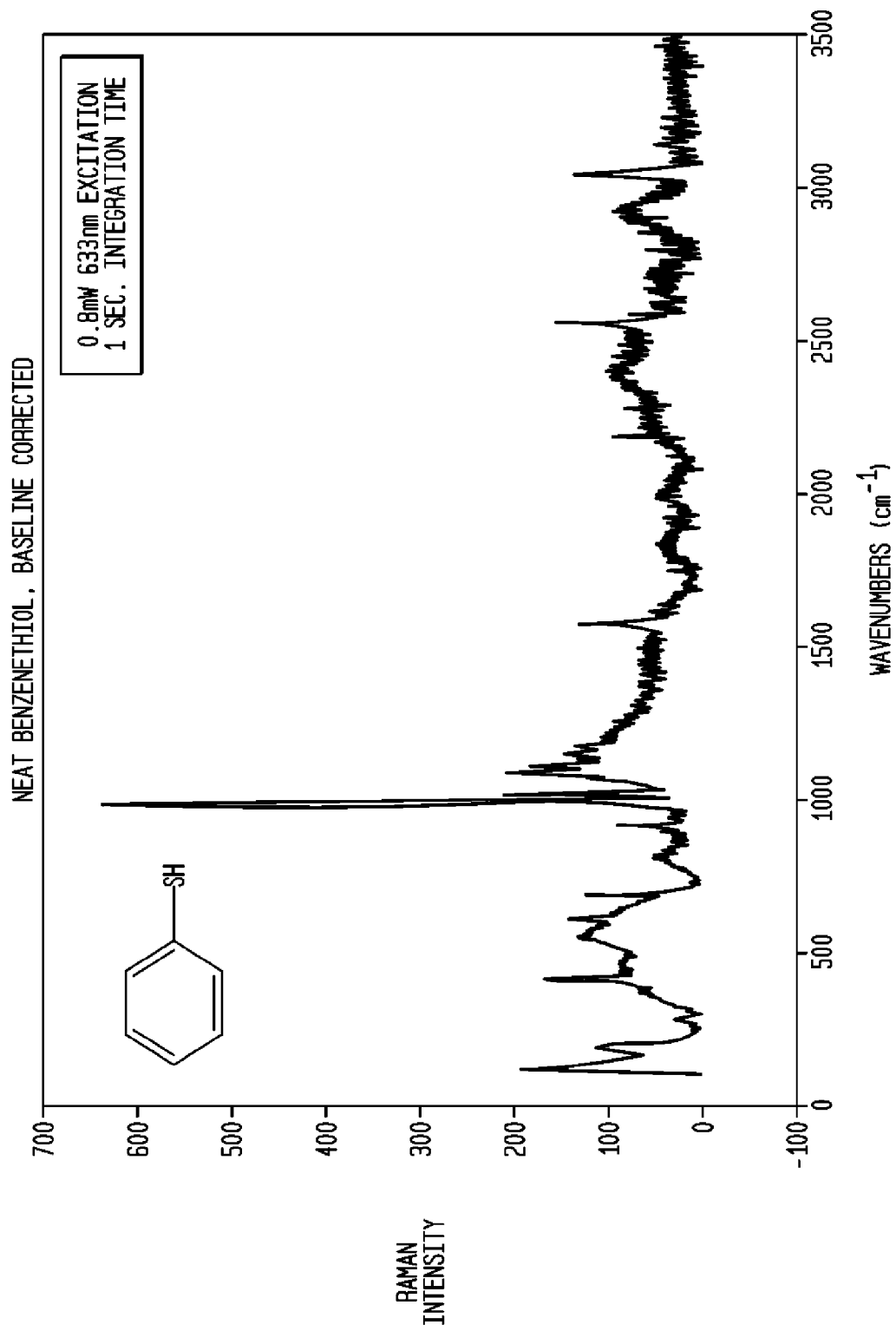
FIG. 8B is a control Raman spectrum of neat, bulk Benzenethiol.

A silicon surface was irradiated with a plurality of femtosecond laser pulses with a pulse width of about 100 femtoseconds while the surface was in contact with water such that each surface location was exposed to about 500 laser pulses. In this manner, a plurality of submicron-sized features were formed on the silicon surface. The nanostructured silicon surface was metalized by evaporating silver onto the surface at an evaporation rate of about 1.5 angstroms per second for a time period of about 8.75 minutes. A film of Benzenethiol was disposed on the metalized surface and a Raman spectrum of the Benzenethiol was obtained by employing a commercial Raman spectrometer manufactured by Horiba Jobin Yvon, Inc. of New Jersey, U.S.A., under the trade designation Aramis. This Raman spectrum is shown in FIG. 8A. As a control, the Raman spectrum of bulk, neat Benzenthiol was obtained by employing the same spectrometer. The control spectrum is shown in FIG. 8B. A comparison of the spectra presented in FIGS. 8A and 8B indicates that the use of the metal-covered nanostructured silicon surface results in an enhancement of the order of $10^{10}$ in the signal-to-noise ratio of the Raman spectrum.

EXAMPLE 2

A polymeric sensing substrate having a surface with submicron-sized ridges was formed by utilizing a hard-poly (dimethylsiloxane) polymer. The polymer was employed to replicate the submicron-sized features formed on a surface of a silicon wafer via exposure to femtosecond pulses, in a manner discussed above in connection with Example 1. More specifically, a surfactant, namely, (tridecafluoro-1,1,2,2-tetrahydrooctyl)-1-trichlorosilane, was applied to the nanostructured silicon surface and a film of the polymer (having an approximate thickness of about 1 mm) was poured on that surface. The polymer was subsequently cured via heat treatment at a temperature of about 40 deg. Celsius for a duration of about 8 hours, to form a negative polymeric mold of the nanostructured semiconductor surface. The cured polymer was removed from the semiconductor substrate, and the polymeric surface exhibiting nanosized ridges was metalized, via thermal deposition, by evaporating silver onto the surface at an evaporation rate of about 1.5 angstroms per second for a time period of about 8.75 minutes to generate a polymeric sensing substrate with a surface exhibiting metallic mesostructures.

Figure 9A:
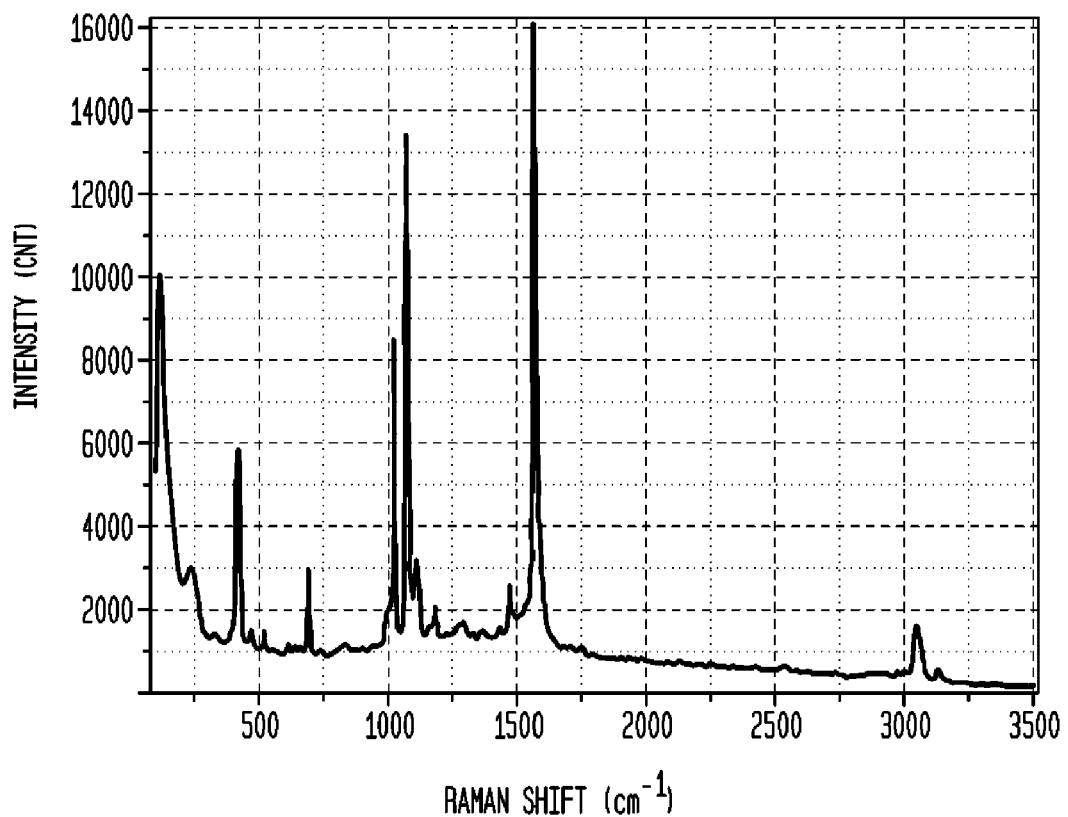
FIG. 9A is a surface enhanced Raman spectrum of a monolayer of Benzenethiol disposed on a structured conductive surface of a polymeric sensing substrate, which is obtained by back illumination of the substrate.

The polymeric sensing substrate was employed to obtain Raman spectrum of a self assembled monolayer (SAM) of benzenethiol. By way of example, FIG. 9A shows such a spectrum that was collected using a Jobin Yvon LabRam ARAMIS Raman microscope with 633 nm HeNe laser excitation. The microscope was operated with no pinhole in place (that is, not in confocal mode). A 10×, 0.25NA objective was employed to focus and collect the light. The integration (collection) time was about 1 second. The reference sample was a 500 micron thick cell of neat benzenethiol. The spectrum shown in FIG. 9A was obtained by utilizing back illumination (i.e., illumination of the back surface of the polymeric substrate).

Figure 9B:
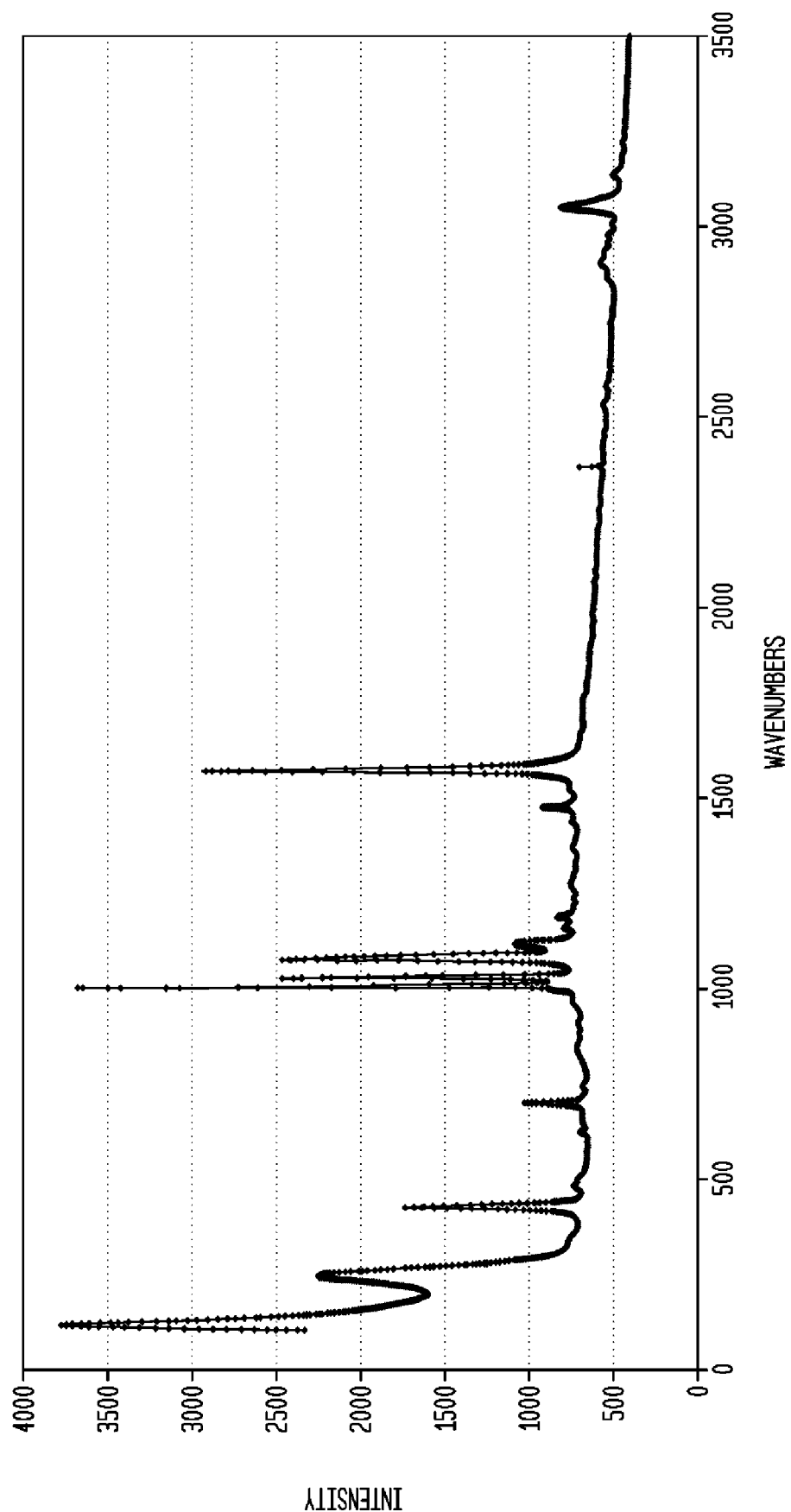
FIG. 9B is a surface enhanced Raman spectrum of a monolayer of Benzenethiol disposed on a structured conductive surface of a polymeric sensing substrate, which is obtained by front illumination of the substrate.

Raman spectrum of a self assembled monolayer of Benzenethiol was also obtained by employing front illumination of the polymeric sensing substrate (illumination of the metallic surface). This spectrum is shown in FIG. 9B. In addition, Raman spectrum of a self assembled monolayer (SAM) of benzenthiol disposed on a nanostructured silicon substrate was also acquired. These spectra were utilized to compare Raman scattering molecular cross section enhancement factor (EF) among these three ways of obtaining Raman spectra in accordance with the teachings of the invention.

A self-assembled monolayer (SAM) of benzenethiol was used to quantify the number of molecules present on the structured surfaces. The molecular packing density of benzenethiol on a silver surface is known to be approximately $4 \times 10^{14}$ cm$^{-2}$. For the Raman spectra of the SAM on the silver coated structured surfaces, the integrated peak intensity of a single Raman band was normalized with a Raman band from the spectrum of a sample of neat benzenethiol so as to derive an enhancement factor of the scattering cross section per individual molecule. With knowledge of the neat sample's refractive index, molar volume, and probed volume, the EF of the various substrates were determined. Table 1 below shows the substrate type and the corresponding cross section factor versus Raman band.

TABLE 1

| Substrate | EF (1000 cm$^{-1}$ band) | EF (1572 cm$^{-1}$ band) |
| --- | --- | --- |
| structured silicon | $1.88 \times 10^{10}$ | $1.49 \times 10^{11}$ |
| structured polymer (front illumination) | $1.65 \times 10^{10}$ | $1.07 \times 10^{11}$ |
| structured polymer (back illumination) | $2.45 \times 10^{10}$ | $7.76 \times 10^{10}$ |

The variation in enhancement factor versus Raman band is understood to be due to the tensorial nature of the molecular polarizability ($\alpha$) and the inhomogeneous molecular orientation distribution of the SAM on the silver coated substrates. The calculation (normalization) method used here involves integrating over the volume of a focused Gaussian beam. The above table shows that significant enhancements in EF can be obtained with both structured silicon as well as structured polymeric substrates.

It should be understood that the enhancement factor can be defined differently than that discussed above, which can lead to different numerical values for the enhancement factor. Regardless, the above exemplary data shows that a significant enhancement factor can be achieved by the use of the structured sensing substrates. By way of example, an article entitled "Surface Enhanced Raman Scattering Enhancement Factors: A Comprehensive Study," authored by Le Ru et al. and published in J. Phys. Chem. C 2007, 111, 13794-13803 describes various definitions of SERS enhancement factors. This article in herein incorporated by reference in its entirety Those having ordinary skill in the art will appreciate that various modifications can be made to the above embodiments without departing from the scope of the invention.

What is claimed is:

1. A system for use in product packaging, comprising
   a sensing substrate coupled to a package such that a front surface thereof is in contact with a portion of a product stored in said package and a back surface thereof is accessible to an environment external to the package,
   a radiation source adapted to direct radiation to said back surface of the substrate, and
   a detector adapted to detect radiation returning from said substrate in response to illumination by said radiation source.

2. The system of claim 1, wherein said product comprises a fungible product.

3. The system of claim 1, further comprising an analyzer operating on said detected radiation to determine a selected characteristic of said product stored in the package.

4. The system of claim 3, wherein said analyzer comprises a Raman spectrometer operating on said detected radiation to generate one or more Raman spectra of at least one constituent of said food product.

5. The system of claim 4, wherein said analyzer compares said one or more Raman spectra with one or more reference spectra to determine said selected characteristic.

6. The system of claim 1, wherein said front surface of the sensing substrate comprises a plurality of nano-sized ridges having a metallic coating disposed thereon.

7. The system of claim 6, wherein said metallic coating comprises a discontinuous metallic coating.

8. The system of claim 6, wherein said metallic coating comprises a substantially continuous metal layer.

9. The system of claim 8, wherein said metallic layer has a thickness in a range of about 10 nm to about 1000 nm.

10. The system of claim 1, further comprising an identification tag disposed on said package for identifying the product stored therein.

11. The system of claim 10, wherein said identification tag is optically readable.

12. The system of claim 11, wherein said identification tag comprises a bar code.

13. The system of claim 3, wherein said analyzer further comprises memory for storing said one or more reference spectra.

14. A method of non-invasively determining a characteristic of a product stored in a package, comprising
    coupling a polymeric sensing substrate to the package such that a sensing surface of said substrate is in contact with the product and an opposed surface of said substrate is accessible via an external environment,
    directing radiation to said accessible surface from an external radiation source,
    detecting at least a portion of radiation returning from the substrate in response to said radiation from the source.

15. The method of claim 14, wherein said detecting step comprises obtaining a surface enhanced Raman spectrum of at least one Raman active constituent of said product.

16. The method of claim 14, wherein said product comprises a fungible product.

17. The method of claim 14, wherein said opposed surface of the substrate is accessible to the external environment through a portion of the package.

18. An optical sensing system, comprising
    a chamber adapted for containing an analyte,
    a polymeric substrate having a plurality of ridges and a metallic coating covering at least a portion of said ridges on a front side thereof, said substrate being coupled to the chamber such that at least a portion of said metallic coating is exposed to the chamber and at least a portion of the back side of the substrate is accessible via an external environment,
    a radiation emitter optically coupled to said chamber so as to direct radiation to said accessible portion of the substrate back side, and
    a detector coupled to the chamber and adapted to detect at least a portion of radiation returning from said substrate in response to illumination by said emitter.

19. The system of claim 18, wherein said emitter generates radiation for inducing a surface enhanced Raman scattering signal from at least one Raman active constituent of said analyte.

20. The system of claim 19, wherein said detector detects said Raman scattering signal.

21. The system of claim 18, wherein said metallic coating comprises a discontinuous metal coating.

* * * * *